United States Patent
Wang et al.

(10) Patent No.: US 10,687,581 B2
(45) Date of Patent: Jun. 23, 2020

(54) ANTISTATIC SHOE WITH A CONDUCTIVE MEMBER

(71) Applicant: NEW PROCESS CORP., Taichung (TW)

(72) Inventors: San-Huai Wang, Taichung (TW); Tzu-Yang Wang, Taichung (TW)

(*) Notice: Subject to any disclaimer, the term of this patent is extended or adjusted under 35 U.S.C. 154(b) by 160 days.

(21) Appl. No.: 16/046,353

(22) Filed: Jul. 26, 2018

(65) Prior Publication Data

US 2018/0332922 A1 Nov. 22, 2018

Related U.S. Application Data

(63) Continuation-in-part of application No. 15/241,435, filed on Aug. 19, 2016, now Pat. No. 10,159,303.

(51) Int. Cl.
| | |
|---|---|
| *A43B 13/12* | (2006.01) |
| *A43B 7/36* | (2006.01) |
| *A43B 1/04* | (2006.01) |
| *A43B 5/02* | (2006.01) |
| *A43B 3/00* | (2006.01) |
| *A43B 7/32* | (2006.01) |
| *A61B 5/00* | (2006.01) |

(52) U.S. Cl.
CPC .............. *A43B 7/36* (2013.01); *A43B 1/04* (2013.01); *A43B 5/02* (2013.01); *A43B 13/12* (2013.01); *A43B 3/0005* (2013.01); *A43B 7/32* (2013.01); *A61B 5/6807* (2013.01); *Y10S 57/901* (2013.01)

(58) Field of Classification Search
USPC .................................................. 361/212, 220
See application file for complete search history.

(56) References Cited

U.S. PATENT DOCUMENTS

2002/0181183 A1* 12/2002 Lee .......................... A43B 7/36
361/223

FOREIGN PATENT DOCUMENTS

TW           M361917 U       8/2009

* cited by examiner

*Primary Examiner* — Danny Nguyen
(74) *Attorney, Agent, or Firm* — Wang Law Firm, Inc.

(57) ABSTRACT

An antistatic shoe with a conductive member includes: a sole made of conductive material; a conductive member having a first conductive portion, a resistor and a second conductive portion; and an insole disposed on the sole. The conductive member is sandwiched between the insole and the sole, and the insole has a conductive portion made of conductive material, wherein the resistor is electrically connected to the first conductive portion and the second conductive portion, the conductive portion is electrically connected to the first conductive portion and disposed in an offset manner to the second conductive portion, and the second conductive portion is electrically connected to the sole. Or, an insulating member made of a non-conductive material is provided between the insole and the conductive member to cover the second conductive portion and the resistor.

8 Claims, 10 Drawing Sheets

ANTISTATIC SHOE WITH A CONDUCTIVE MEMBER

CROSS REFERENCE TO RELATED APPLICATION

This application is a continuation in part of U.S. patent application Ser. No. 15/241,435, which claims the earlier filing date of Aug. 19, 2016, the entire specification of which is incorporated herein by reference.

BACKGROUND

Field of the Invention

The present invention relates to a shoe, and more particularly to an antistatic shoe with a conductive member.

Related Prior Art

Figure 1:
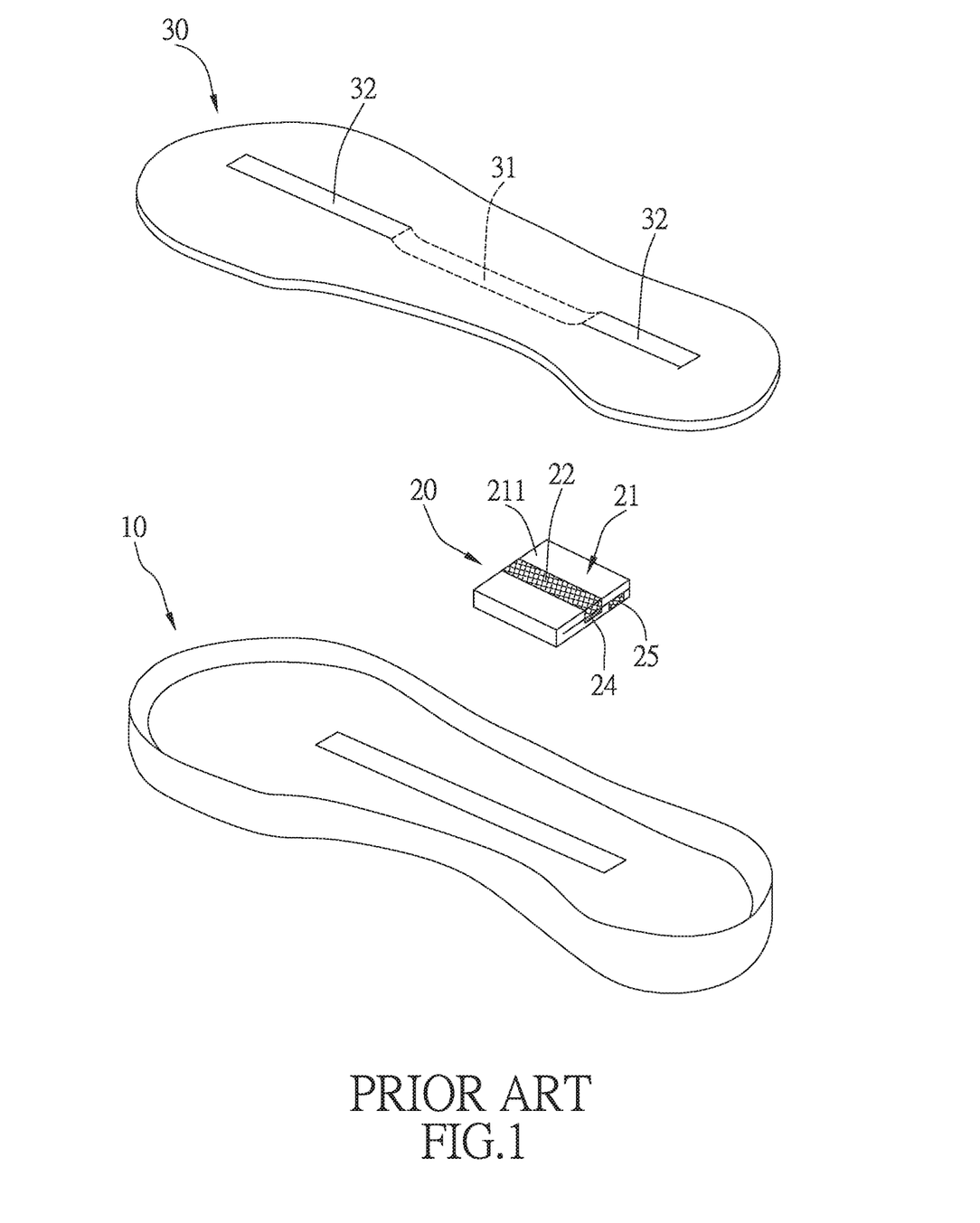
FIG. 1 is an exploded view of a conventional antistatic shoe.

A conventional antistatic shoe as shown in FIG. 1 comprises: a sole 10, a conductive member 20, and an insole 30. The conductive member 20 is disposed between the sole 10 and the insole 30. The sole 10 is made of a conductive material. The insole 30 has a first conductive strip 31 and two second conductive strips 32. The first conductive strip 31 is disposed on one side of the insole 30, the two second conductive strips 32 are disposed on the other side opposite to the first conductive strip 31, and the first conductive strip 31 and the second conductive strips 32 are electrically connected to each other.

Figure 3:
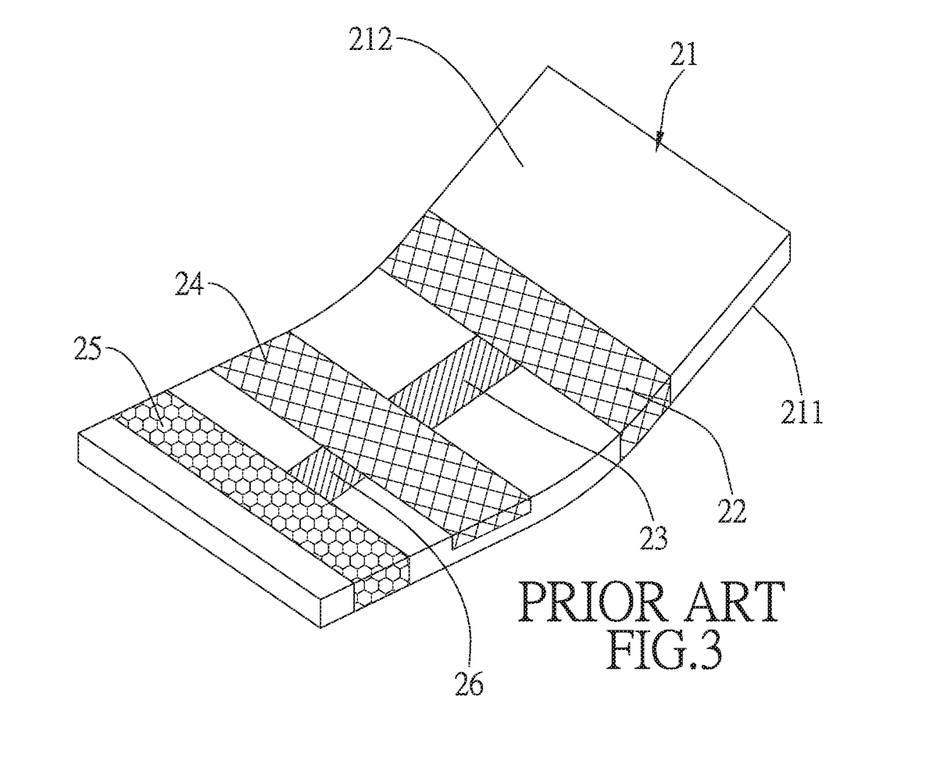
FIG. 3 is a perspective view showing the unfolded state of the conductive member of the conventional antistatic shoe.
Figure 4:
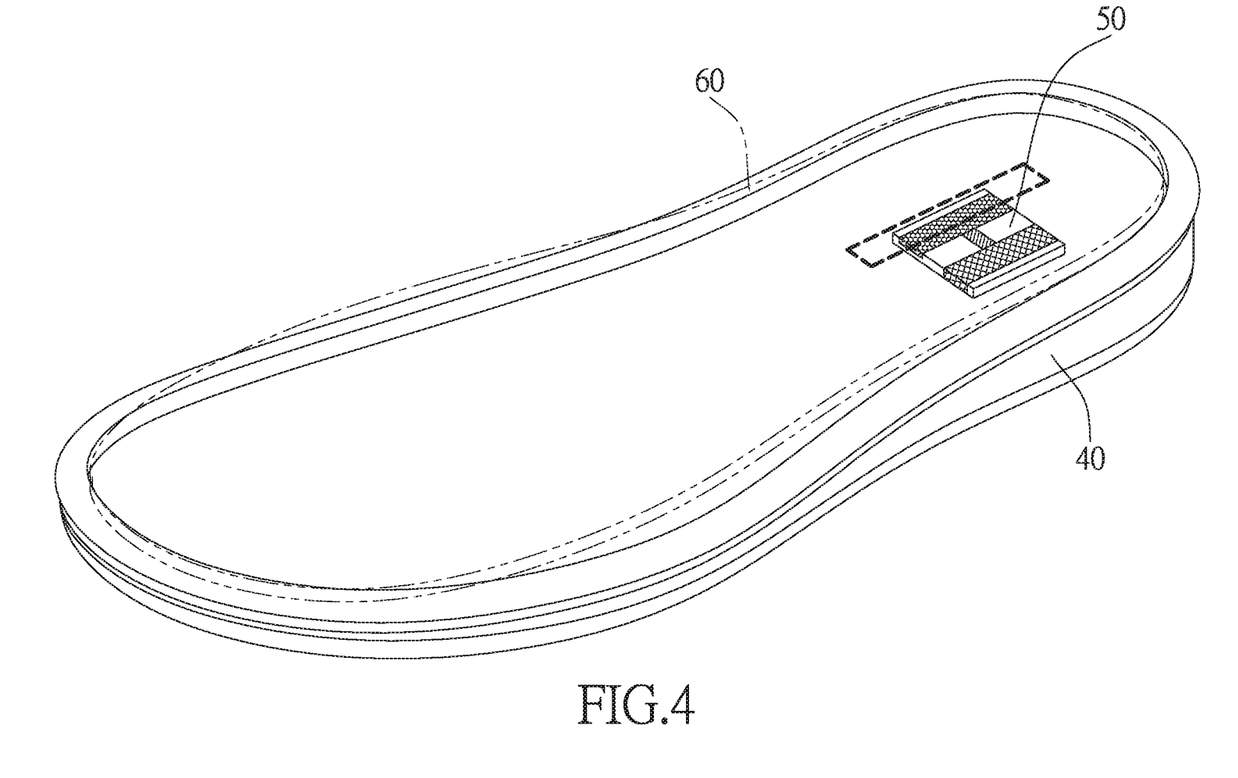
FIG. 4 is an assembly view of the sole, the conductive member and the insole of the preferred embodiment of the invention.
Figure 5:
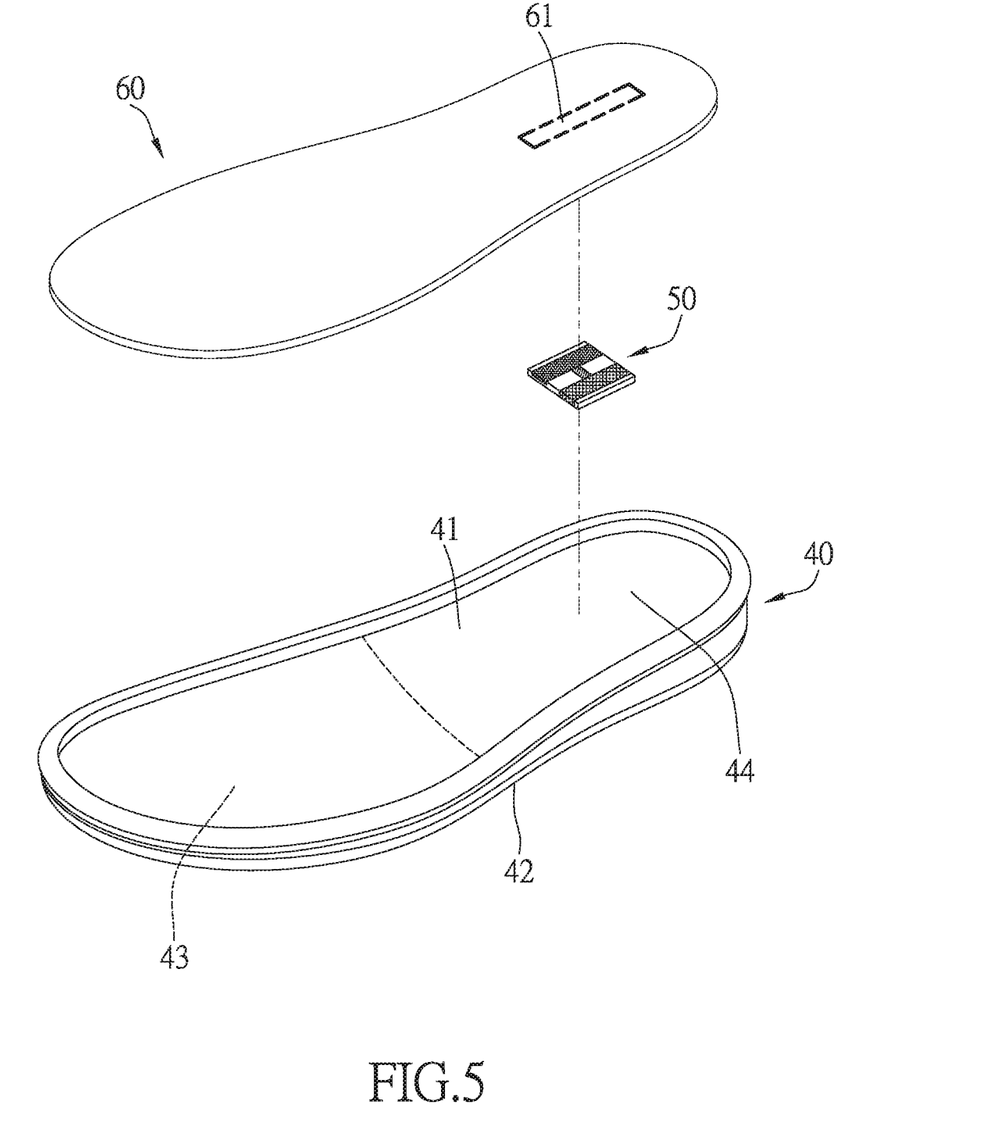
FIG. 5 is an exploded view of the antistatic shoe in accordance with the preferred embodiment of the invention.
Figure 6:
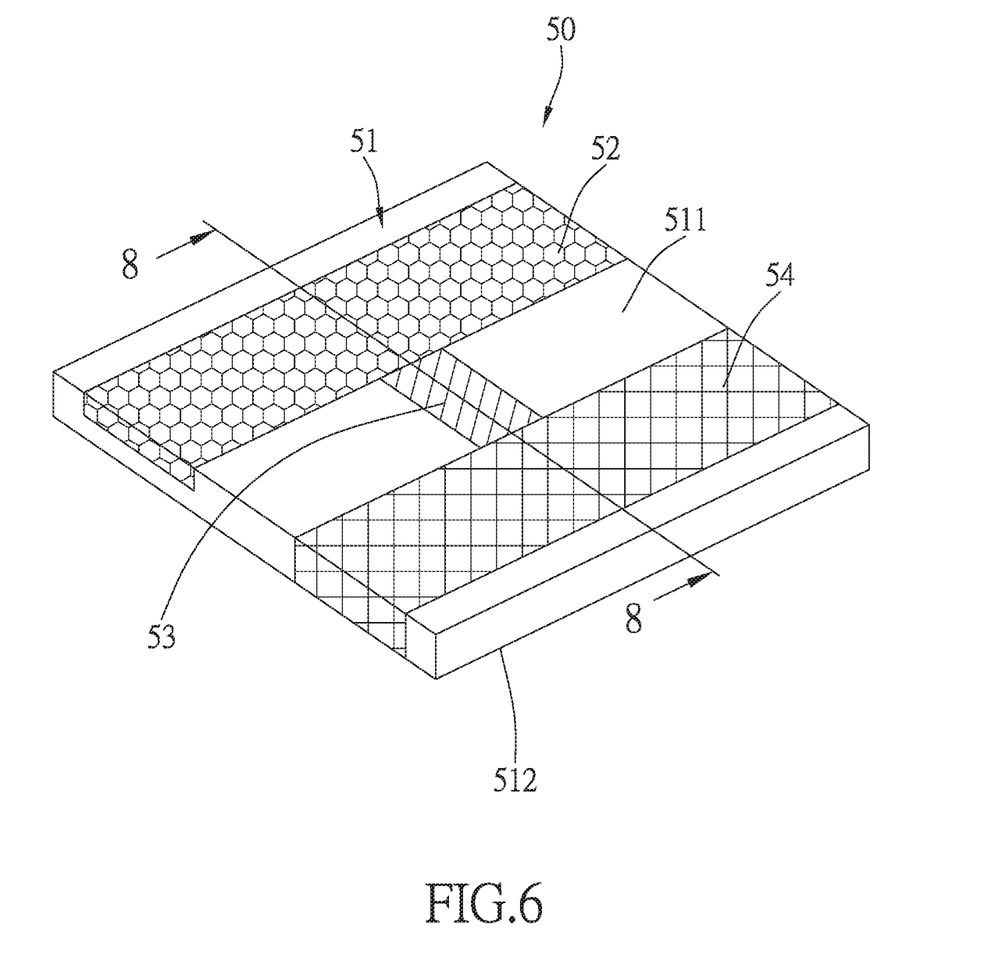
FIG. 6 is a perspective view of the conductive member in accordance with the preferred embodiment of the invention.
Figure 7:
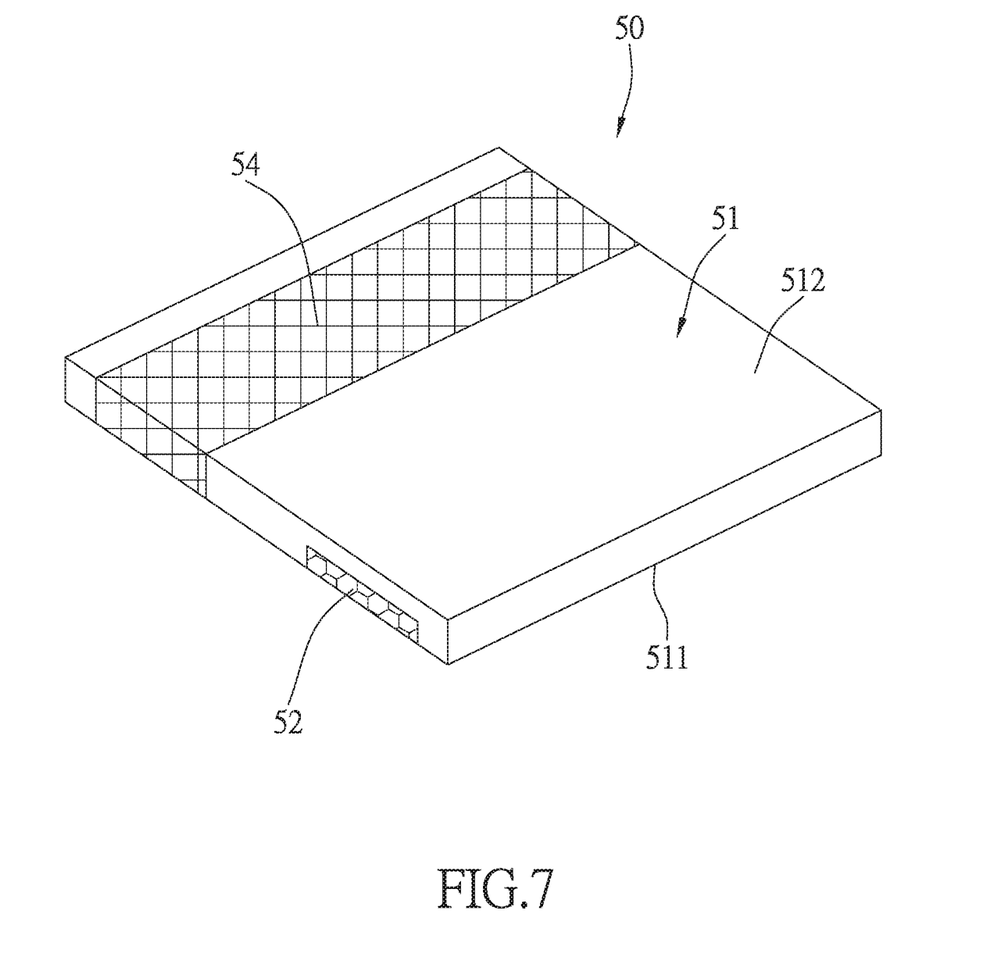
FIG. 7 is a perspective view of the invention showing that the conductive member is disposed on the second surface.
Figure 8:
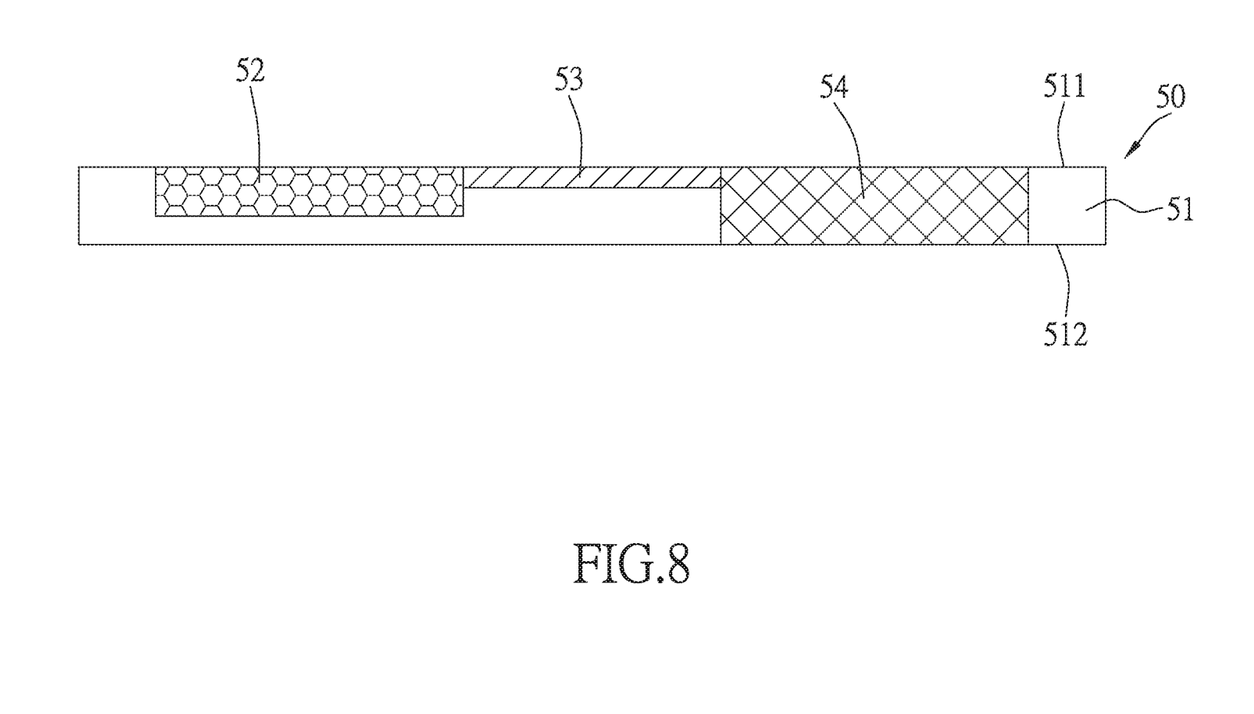
FIG. 8 is a cross sectional view taken along the line 8-8 of FIG. 6.

FIG. 3 is a perspective view of the conductive member 20 after being spread out. The conductive member 20 includes a body 21 which has a first surface 211 and an opposite second surface 212. The conductive member 20 has a first conductive portion 22, a second conductive portion 23, a third conductive portion 24, a fourth conductive portion 25, and a resistor 26 disposed on the body 21. The first conductive portion 22 is connected to the first surface 211 and the second surface 212. The second conductive portion 23 is located on the second surface 212 and connected to the first conductive portion 22. The third conductive portion 24 is located on the second surface 212 and connected to the second conductive portion 23. The fourth conductive portion 25 is connected to the first surface 211 and the second surface 212. The resistor 26 is located on the second surface 212 and connected to the third conductive portion 24 and the fourth conductive portion 25.

Figure 2:
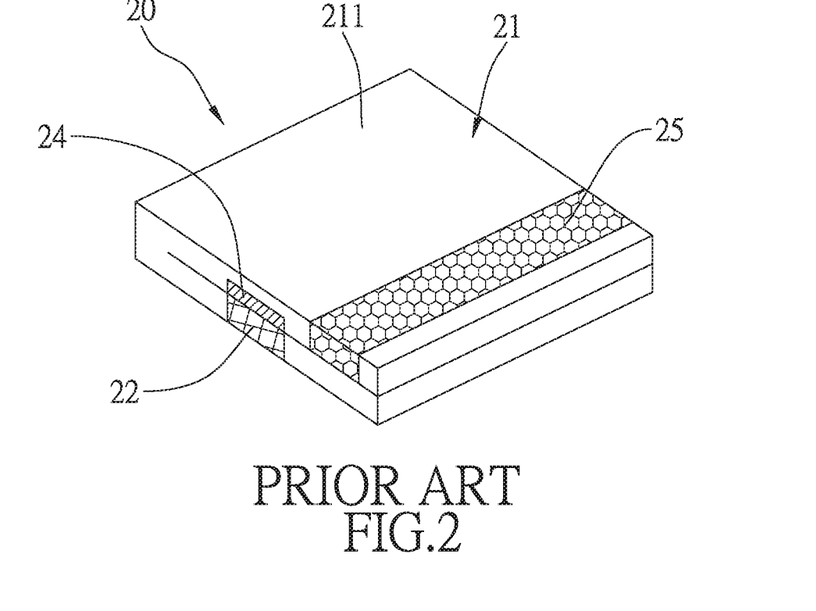
FIG. 2 is a perspective view showing that the conductive member of the conventional antistatic shoe is folded at the second surface.

The folded state of the conductive member 20 is as shown in FIGS. 1 and 2, and the second surface 212 of the conductive member 20 is overlapped so that the first conductive portion 22 and the third conductive portion 24 are in contact. The folded conductive member 20 is disposed between the sole 10 and the insole 30, so that the first conductive portion 22 on the first surface 211 is electrically connected to the first conductive strip 31, and the fourth conductive portion 25 on the first surface 211 is electrically connected to the sole 10.

After the user's foot comes into contact with the two second conductive strips 32 of the insole 30, static electricity accumulated in the user's body is conducted to the first conductive strip 31 through the two second conductive strips 32, and finally transmitted to the sole 10 through the first conductive strip 31, the first conductive portion 22, the second conductive portion 23, the third conductive portion 24, the resistor 26, and the fourth conductive portion 25, so as to allow the charge to be introduced into the ground to safely discharge the static electricity accumulated in the user's body.

In particular, the resistor 26 can prevent the accumulated charge in the human body from being released quickly and rapidly, thereby destroying electronic components or creating sparks, which can cause danger or discomfort, so that the user is prevented from having a painful feeling due to an electrostatic reaction when discharging the electric charge.

However, the structure of the conductive member 20 is complex, and not only is the conductive member 20 more difficult to manufacture, but its manufacturing cost is relatively high, which makes it impossible to be popularized in the market, and this is what the present invention intends to improve.

The present invention has arisen to mitigate and/or obviate the afore-described disadvantages.

SUMMARY

One objective of the present invention is to solve the problem that the structure of the conductive member is complicated and the manufacturing cost is increased.

Another objective of the present invention is to allow the charges to be smoothly released by the regulation of the resistor, thus preventing the damage to electronic components or occurrence of sparks or discomfort caused by instantaneous and massive release of the charges accumulated in the user's body.

To achieve the above objectives, an antistatic shoe with a conductive member in accordance with one embodiment of the invention comprises:

a sole made of conductive material;

the conductive member being disposed on the sole, and including: a body, and a first conductive portion, a resistor and a second conductive portion disposed on the body, wherein the body has a first surface, and a second surface attached to the sole, the first conductive portion is disposed on the first surface, the resistor is disposed on the first surface and connected to the first conductive portion, so that the resistor is electrically connected to the first conductive portion, the second conductive portion is connected to the first surface and the second surface, the second conductive portion on the first surface is electrically connected to the resistor and the sole; and an insole disposed on the sole, wherein the conductive member is sandwiched between the insole and the sole, the insole has a conductive portion made of conductive material, the conductive portion is electrically connected to the first conductive portion and disposed in an offset manner to the second conductive portion.

To achieve the above objectives, an antistatic shoe with a conductive member in accordance with another embodiment of the invention comprises:

a sole made of conductive material;

the conductive member being disposed on the sole, and including: a body, and a first conductive portion, a resistor and a second conductive portion disposed on the body, wherein the body has a first surface, and a second surface attached to the sole, the first conductive portion is disposed on the first surface, the resistor is disposed on the first surface and connected to the first conductive portion, so that the resistor is electrically connected to the first conductive portion, the second conductive portion is connected to the first surface and the second surface, the second conductive portion on the first surface is electrically connected to the resistor and the sole;

an insole disposed on the sole, wherein the conductive member is sandwiched between the insole and the sole, the insole has a conductive portion made of conductive material, the conductive portion is electrically connected to the first conductive portion; and an insulating member made of a non-conductive material provided between the insole and the conductive member to cover the second conductive portion and the resistor.

Preferably, the resistor has a resistance of 1 MΩ to 10 MΩ.

Preferably, the resistor is a surface mount device.

The conductive member of the present invention has a simple structure since it is only provided with the body, the first conductive portion, the resistor, and the second conductive portion. Besides, the offset arrangement of the resistor and the second conductive portion with respect to the conductive portion allows the electric charges to be transmitted sequentially through the conductive portion, the first conductive portion, the resistor, the second conductive portion and the insole, thereby preventing static electricity, and further preventing the damage to electronic components or occurrence of sparks or discomfort caused by instantaneous and massive release of the charges accumulated in the user's body.

In another embodiment, the insulating member prevents electric connection of the second conductive portion and the resistor to the conductive portion, so as to ensure that the accumulated electric charges in the user's body can be transmitted sequentially through the conductive portion, the first conductive portion, the resistor, the second conductive portion, the insole and the sole.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

DETAILED DESCRIPTION

The present invention will be clearer from the following description when viewed together with the accompanying drawings, which show, for purpose of illustrations only, the preferred embodiment in accordance with the present invention.

Referring to FIGS. 4-8, an antistatic shoe with a conductive member in accordance with the preferred embodiment of the invention comprises: a sole 40, the conductive member 50 and an insole 60.

The sole 40 is made of an electrically conductive material, and includes a top surface 41 and a bottom surface 42. The bottom surface 42 is provided for stamping on the ground. The sole 40 has a front end 43 and a rear end 44.

The conductive member 50 is disposed on the top surface 41, and includes: a body 51, and a first conductive portion 52, a resistor 53, and a second conductive portion 54 disposed on the body 51. The body 51 has a first surface 511, and an opposite second surface 512 attached to the top surface 41. The first conductive portion 52 is disposed on the first surface 511, the resistor 53 is disposed on the first surface 511 and connected to the first conductive portion 52, so that the resistor 53 is electrically connected to the first conductive portion 52. The second conductive portion 54 is connected to the first surface 511 and the second surface 512. The second conductive portion 54 penetrates or surrounds the body 51, so that the second conductive portion 54 is exposed on the first surface 511 and the second surface 512. The second conductive portion 54 on the first surface 511 is electrically connected to the resistor 53 and the sole 40.

Preferably, the conductive member 50 is disposed at the front end 43 or the rear end 44.

The insole 60 is mounted on the sole 40, the conductive member 50 is sandwiched between the insole 60 and the sole 40, and the first surface 511 of the conductive member 50 is attached to the insole 60. The insole 60 has a conductive portion 61 made of an electrically conductive material and provided for contacting the human body, and the conductive portion 61 is electrically connected to the first conductive portion 52. The conductive portion 61 is disposed in an offset manner to the second conductive portion 54.

What mentioned above are the structural configurations of the present invention and their connection relations, and the use of the present invention is described as follows:

Referring to FIGS. 4-8, when the user steps on the insole 60 and comes into contact with the conductive portion 61, and charges accumulated in the user's body are conducted to the first conductive portion 52 through the conductive portion 61. Charges are conducted to the sole 40 through the resistor 53 and the second conductive portion 54, so that the charges accumulated in the user's body are finally transmitted to the ground.

Since the conductive portion 61 is arranged in an offset manner with respect to the second conductive portion 54 and the resistor 53, which allows the charges in the user's body to pass through the first conductive portion 52, the resistor 53, and the second conductive portion 54 sequentially. Therefore, the present invention not only has a simple structure to reduce manufacturing cost, but also enables the charges accumulated in the user's body to be stably conducted through the regulation of the resistor 53, thereby preventing the damage to electronic components or occurrence of sparks or discomfort caused by instantaneous and massive release of the charges accumulated in the user's body.

Figure 9:
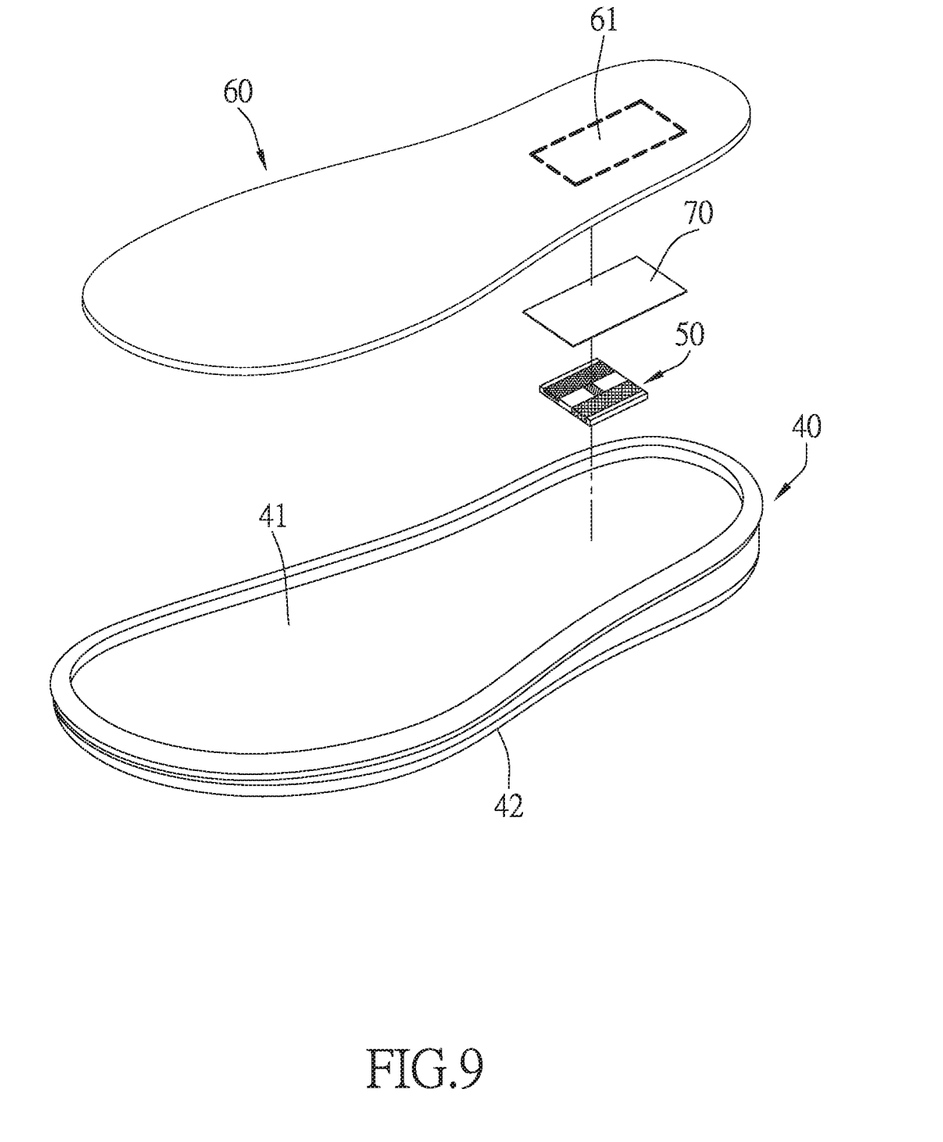
FIG. 9 is an exploded view of the antistatic shoe in accordance with the another preferred embodiment of the invention.
Figure 10:
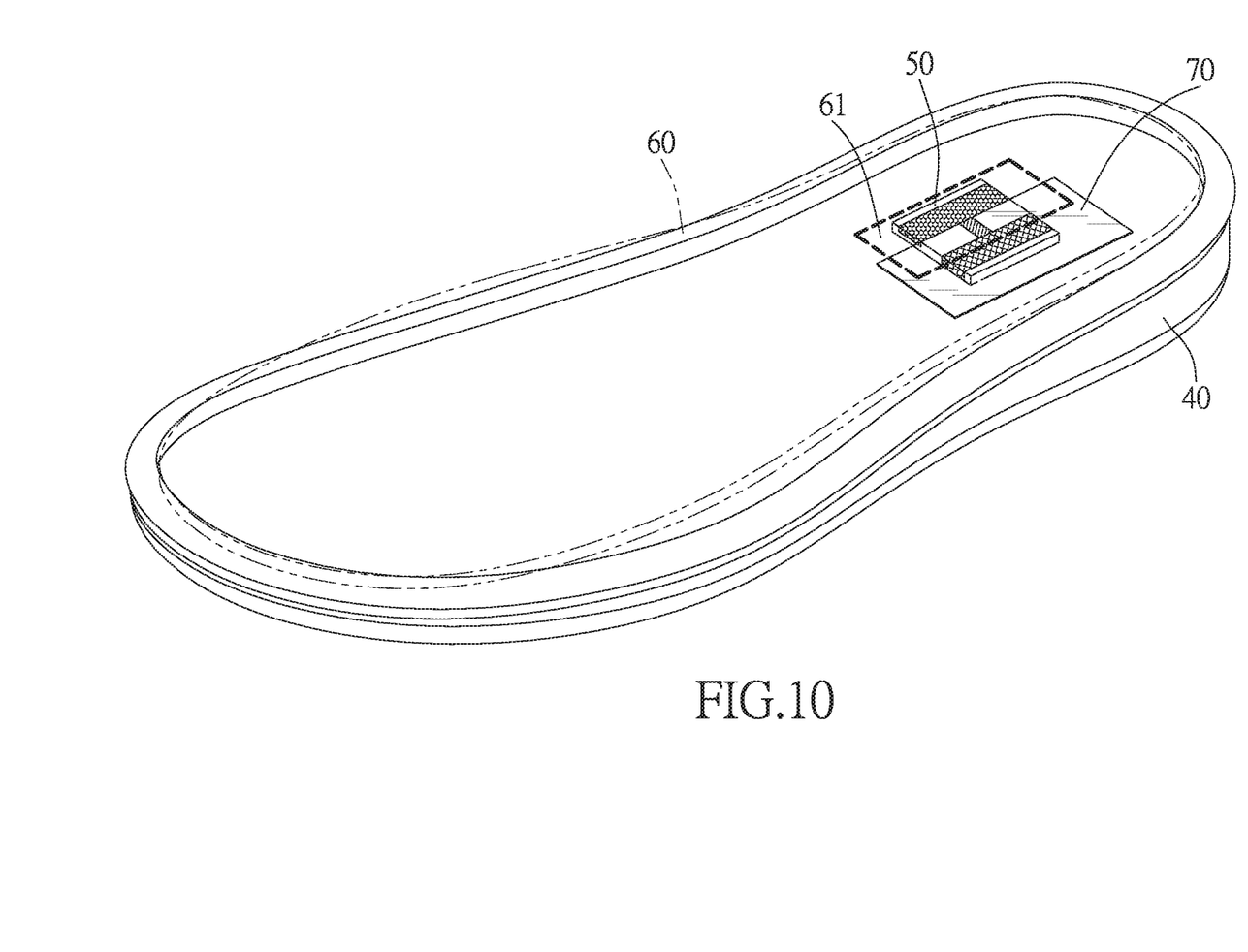
FIG. 10 is an assembly view of the sole, the conductive member and the insole of the another preferred embodiment of the invention.
Figure 11:
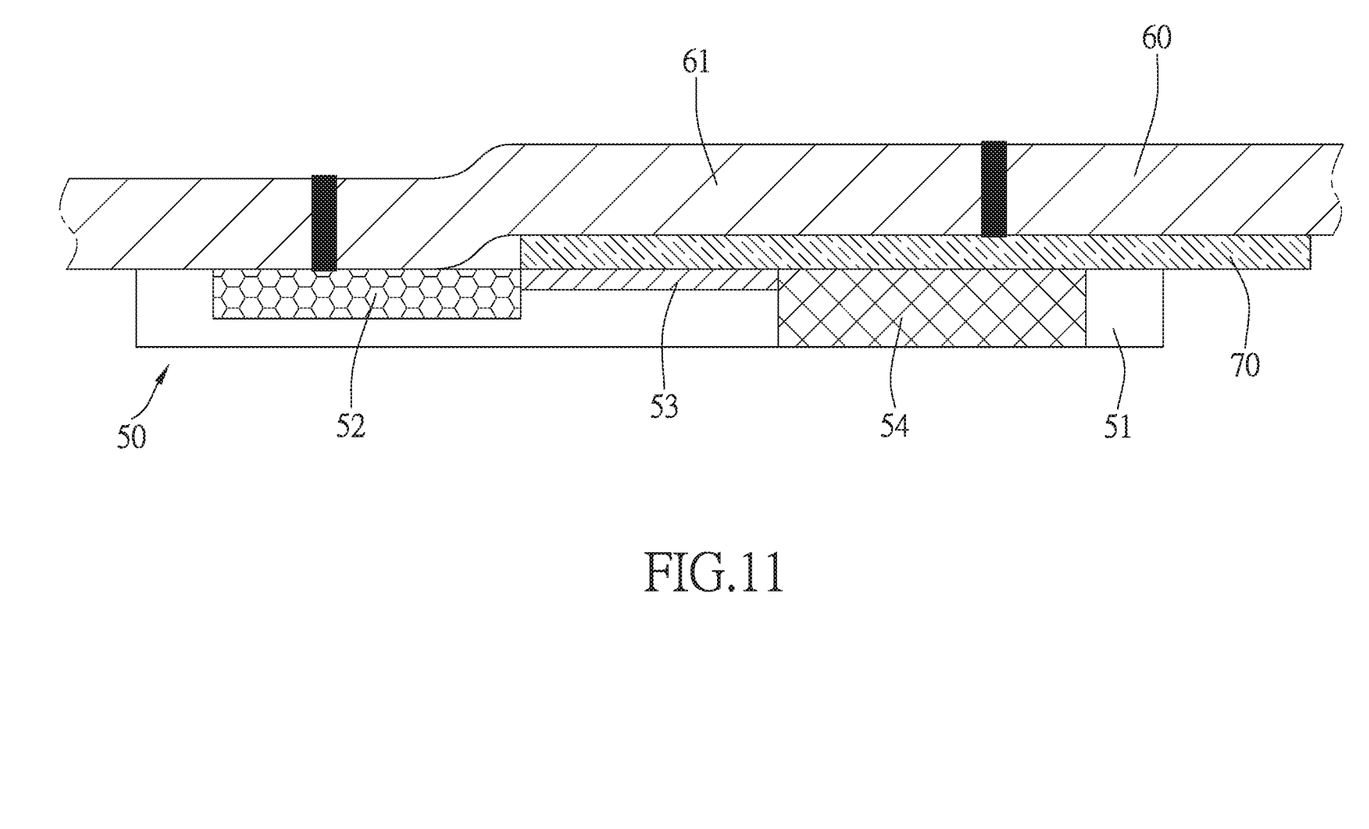
FIG. 11 is a cross sectional view of the another preferred embodiment of the invention.

Referring to FIGS. 9-11, in another preferred embodiment of the present invention, an insulating member 70 is further provided between the insole 60 and the conductive member 50, and is made of a non-conductive material. The insulating member 70 covers the second conductive portion 54 and the resistor 53, so that the second conductive portion 54 and the resistor 53 do not come into contact with the conductive portion 61.

The insulating member 70 can block the second conductive portion 54 and the resistor 53 from contacting the conductive portion 61, thereby preventing electric connection of the second conductive portion 54 and the resistor 53 with the conductive portion 61, so as to ensure that the accumulated electric charges in the user's body can be transmitted sequentially through the conductive portion 61, the first conductive portion 52, the resistor 53, the second conductive portion 54 and the sole 40. When the charges are finally transmitted to the ground through the resistor 53, since the resistor 53 allows only a relatively small amount of charges to pass through, during the charge release process, the regulation of the resistor 53 allows the charges to be transmitted smoothly, thereby preventing the damage to electronic components or occurrence of sparks or discomfort caused by instantaneous and massive release of the charges accumulated in the user's body.

More preferably, the insulating member 70 covers the second conductive portion 54 and the resistor 53 to prevent electric connection of the second conductive portion 54 and the resistor 53 to the conductive portion 61. During manufacturing, the second conductive portion 54 and the resistor 53 do not need to be specifically disposed in an offset or staggered manner with respect to the conductive portion 61 since the insulating member 70 can disconnect the second conductive portion 54 and the resistor 53 from the conductive portion 61, so as to ensure that the accumulated electric charges in the user's body can be transmitted sequentially through the conductive portion 61, the first conductive portion 52, the resistor 53, the second conductive portion 54 and the sole 40.

More preferably, in the foregoing two embodiments, the resistor 53 is a surface mount device and has a resistance of 1 MΩ to 10 MΩ, thereby reducing the current through the resistor 53 and preventing the damage to electronic components or occurrence of sparks or discomfort caused by instantaneous and massive release of the charges accumulated in the user's body.

The conductive member 50 of the present invention has a simple structure since it is only provided with the body 51, the first conductive portion 52, the resistor 53, and the second conductive portion 54. Besides, the offset arrangement of the resistor 53 and the second conductive portion 54 with respect to the conductive portion 61 allows the electric charges to be transmitted sequentially through the conductive portion 61, the first conductive portion 52, the resistor 53, the second conductive portion 54 and the sole 40, thereby preventing static electricity, and further preventing the damage to electronic components or occurrence of sparks or discomfort caused by instantaneous and massive release of the charges accumulated in the user's body.

In another embodiment, the insulating member 70 prevents electric connection of the second conductive portion 54 and the resistor 53 to the conductive portion 61, so as to ensure that the accumulated electric charges in the user's body can be transmitted sequentially through the conductive portion 61, the first conductive portion 52, the resistor 53, the second conductive portion 54 and the sole 40.

While we have shown and described various embodiments in accordance with the present invention, it is clear to those skilled in the art that further embodiments may be made without departing from the scope of the present invention.

What is claimed is:

1. An antistatic shoe with a conductive member, comprising:
   a sole made of conductive material;
   the conductive member being disposed on the sole, and including: a body, and a first conductive portion, a resistor and a second conductive portion disposed on the body, wherein the body has a first surface, and a second surface attached to the sole, the first conductive portion is disposed on the first surface, the resistor is disposed on the first surface and connected to the first conductive portion, so that the resistor is electrically connected to the first conductive portion, the second conductive portion is connected to the first surface and the second surface, the second conductive portion on the first surface is electrically connected to the resistor and the sole; and
   an insole disposed on the sole, wherein the conductive member is sandwiched between the insole and the sole, the insole has a conductive portion made of conductive material, the conductive portion is electrically connected to the first conductive portion and disposed in an offset manner to the second conductive portion.

2. An antistatic shoe with a conductive member, comprising:
   a sole made of conductive material;
   the conductive member being disposed on the sole, and including: a body, and a first conductive portion, a resistor and a second conductive portion disposed on the body, wherein the body has a first surface, and a second surface attached to the sole, the first conductive portion is disposed on the first surface, the resistor is disposed on the first surface and connected to the first conductive portion, so that the resistor is electrically connected to the first conductive portion, the second conductive portion is connected to the first surface and the second surface, the second conductive portion on the first surface is electrically connected to the resistor and the sole;
   an insole disposed on the sole, wherein the conductive member is sandwiched between the insole and the sole, the insole has a conductive portion made of conductive material, the conductive portion is electrically connected to the first conductive portion; and
   an insulating member made of a non-conductive material provided between the insole and the conductive member to cover the second conductive portion and the resistor.

3. The antistatic shoe with the conductive member as claimed in claim 1, wherein the resistor has a resistance of 1 MΩ to 10 MΩ.

4. The antistatic shoe with the conductive member as claimed in claim 2, wherein the resistor has a resistance of 1 MΩ to 10 MΩ.

5. The antistatic shoe with the conductive member as claimed in claim 1, wherein the resistor is a surface mount device.

6. The antistatic shoe with the conductive member as claimed in claim 2, wherein the resistor is a surface mount device.

7. The antistatic shoe with the conductive member as claimed in claim 1, wherein the sole includes a front end and a rear end, and the conductive member is disposed at the front end or the rear end.

8. The antistatic shoe with the conductive member as claimed in claim 2, wherein the sole includes a front end and a rear end, and the conductive member is disposed at the front end or the rear end.

* * * * *